US012811000B2

(12) United States Patent
Peyrovian

(10) Patent No.: US 12,811,000 B2
(45) Date of Patent: Nov. 24, 2026

(54) SYSTEM AND METHOD FOR ENHANCED MEDICAL DATA TRANSMISSION AND AUTOMATION

(71) Applicant: McKesson Corporation, Irving, TX (US)

(72) Inventor: Cyrus Peyrovian, Cockeysville, MD (US)

(73) Assignee: MCKESSON CORPORATION, Irving, TX (US)

( * ) Notice: Subject to any disclaimer, the term of this patent is extended or adjusted under 35 U.S.C. 154(b) by 245 days.

(21) Appl. No.: 18/330,047

(22) Filed: Jun. 6, 2023

(65) Prior Publication Data

US 2023/0395244 A1 Dec. 7, 2023

Related U.S. Application Data

(60) Provisional application No. 63/349,275, filed on Jun. 6, 2022.

(51) Int. Cl.
*G16H 40/20* (2018.01)
*G06F 16/951* (2019.01)
*G16H 15/00* (2018.01)

(52) U.S. Cl.
CPC ........... *G16H 40/20* (2018.01); *G06F 16/951* (2019.01); *G16H 15/00* (2018.01)

(58) Field of Classification Search
None
See application file for complete search history.

(56) References Cited

U.S. PATENT DOCUMENTS

2011/0257992 A1* 10/2011 Scantland .............. G06Q 10/10 705/2
2015/0127364 A1* 5/2015 Long .............. G06Q 10/063114 705/2
(Continued)

OTHER PUBLICATIONS

S. Ganesh et al., "Web Automation in Health Care," 2019 IEEE International Conference on Innovations in Communication, Computing and Instrumentation (ICCI), Chennai, India, 2019, pp. 28-35. (Year: 2019).*
(Continued)

*Primary Examiner* — Devin C Hein
*Assistant Examiner* — Vincent C Ilagan
(74) *Attorney, Agent, or Firm* — Alston & Bird LLP

(57) ABSTRACT

A method for enhancing and automating medical data transmission is disclosed. The method includes determining if prior authorization is required on an order created from a medical service provider using a backend server that uses stored multiple third-party vendor identification information and communicates with multiple third-party vendors, responsive to determining that the prior authorization is required on the order, submitting a prior authorization request in a standardized data format to a third-party vendor of the multiple third-party vendors, and monitoring a status of the prior authorization request. The order is a healthcare service prescribed by the medical service provider. The prior authorization is a process used by a third-party vendor to verify if a service is medically necessary for a patient. The third-party vendor is at least one of a healthcare insurance company or a utilization management vendor of the healthcare insurance company.

20 Claims, 8 Drawing Sheets

(56) References Cited

U.S. PATENT DOCUMENTS

| | | | | |
|---|---|---|---|---|
| 2017/0116373 | A1* | 4/2017 | Ginsburg | G06F 3/0482 |
| 2020/0110781 | A1* | 4/2020 | Staszak | G06F 16/951 |
| 2020/0160955 | A1* | 5/2020 | Hansen | G16H 15/00 |
| 2020/0410601 | A1* | 12/2020 | Laumeyer | G06F 40/186 |
| 2021/0044637 | A1* | 2/2021 | Lee | H04L 65/4025 |
| 2021/0158924 | A1* | 5/2021 | Stueckemann | G16H 40/60 |
| 2023/0402160 | A1* | 12/2023 | Williams, III | G16H 50/20 |

OTHER PUBLICATIONS

V. Bharadwaj et al., “Empowering mobile healthcare providers via a patient benefits authorization service,” Proceedings Tenth IEEE International Workshop on Enabling Technologies: Infrastructure for Collaborative Enterprises. WET ICE 2001, Cambridge, MA, USA, 2001, pp. 73-78. (Year: 2001).*

* cited by examiner

SYSTEM AND METHOD FOR ENHANCED MEDICAL DATA TRANSMISSION AND AUTOMATION

CROSS REFERENCE TO RELATED APPLICATION

This application claims priority to and the benefit of U.S. Provisional Patent Application Ser. No. 63/349,275 filed on Jun. 6, 2022, the entire disclosure of which is hereby incorporated by reference.

TECHNICAL FIELD

The present disclosure relates generally to enhancing and automating medical data transmission, and more specifically, to automating prior authorization process of medical data.

SUMMARY

A first aspect is a system for enhancing and automating medical data transmission. The system includes a processor and a memory storing instructions. The memory storing instructions cause the processor to execute instructions to: determine, using a backend server that uses stored multiple third-party vendor identification information and communicates with multiple third-party vendors if prior authorization is required on an order that is associated with a healthcare service prescribed by a medical service provider; responsive to determining that the prior authorization is required on the order, submit a prior authorization request in a standardized data format to a third-party vendor of the multiple third-party vendors; and monitor a status of the prior authorization request. The order can be a digital order created by the backend server. The prior authorization can be a process used by a third-party vendor to verify if a service is medically necessary for a patient. The third-party vendor can be at least one of a healthcare insurance company or a utilization management vendor of the healthcare insurance company.

A second aspect is a method for enhancing and automating medical data transmission. The method includes determining, using a backend server that uses stored multiple third-party vendor identification information and communicates with multiple third-party vendors, if prior authorization is required on an order created from a medical service provider; responsive to determining that the prior authorization is required on the order, submitting a prior authorization request to a third-party vendor of the multiple third-party vendors; and monitoring a status of the prior authorization request. The order can be a healthcare service prescribed by the medical service provider. The prior authorization can be a process used by a third-party vendor to verify if a service is medically necessary for a patient. The third-party vendor can be at least one of a healthcare insurance company or a utilization management vendor of the healthcare insurance company.

A third aspect is a non-transitory computer readable medium storing instructions operable to cause one or more processors to automate authorization process of healthcare services. The operations include determining if prior authorization is required on an order that is associated with a healthcare service prescribed by a medical service provider; responsive to determining that the prior authorization is required on the order, submitting a prior authorization request to the third-party vendor; and monitoring a status of the prior authorization request. The order can be a digital order created by the backend server. The prior authorization can be a process used by a third-party vendor to verify if a service is medically necessary for a patient. The third-party vendor can be at least one of a healthcare insurance company or a utilization management vendor of the healthcare insurance company.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
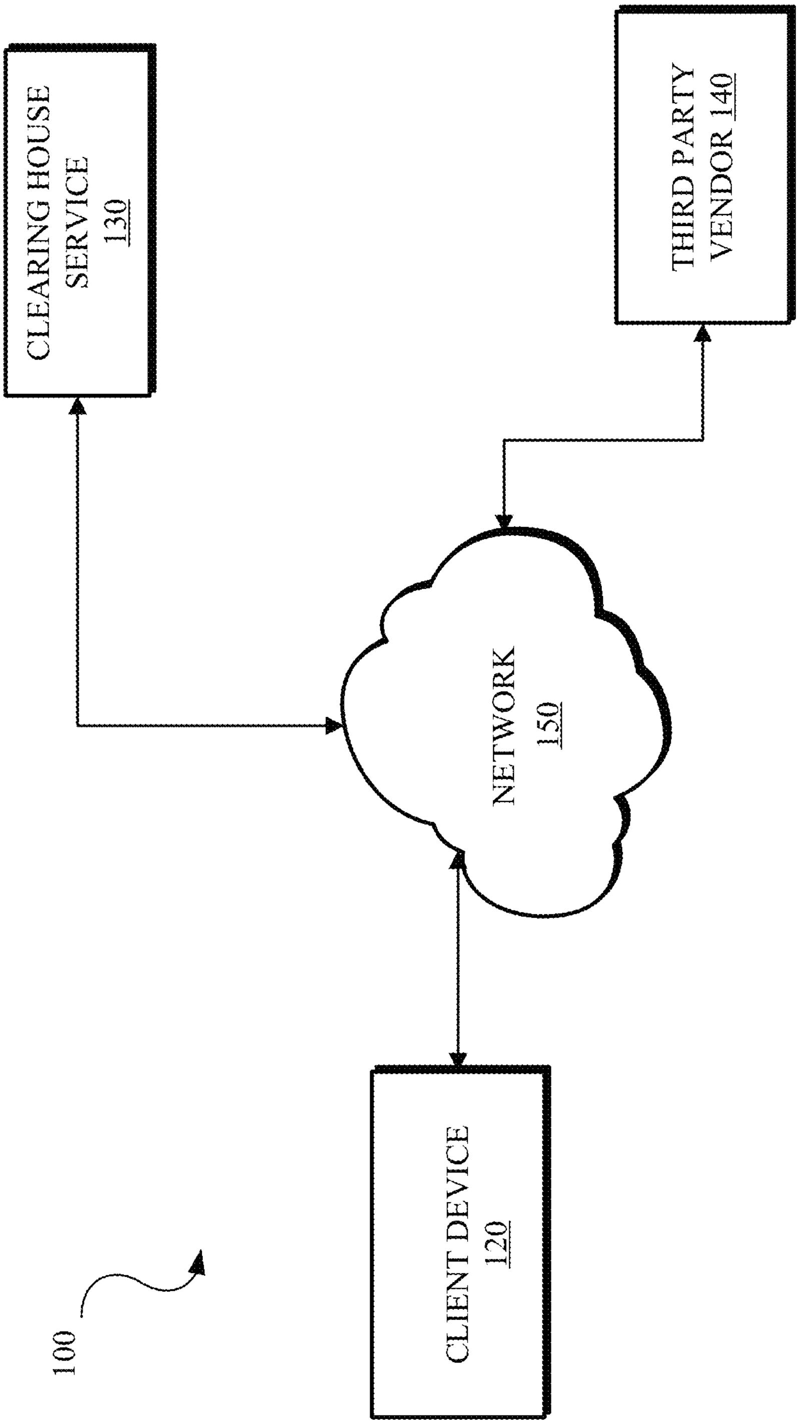
FIG. 1 is a block diagram of an example architecture of a system for automating prior authorizations in accordance with implementations of this disclosure.

The healthcare system employs a variety of intricate administrative processes, which include the verification of a patient's insurance eligibility and the procurement of prior authorizations for specific medical services. These processes are typically undertaken prior to the provision of any medical service to confirm that the service is covered within the patient's insurance plan and is medically requisite. Enhanced medical data transmission and automation have been incorporated into these procedures to streamline operations, utilizing sophisticated data exchange protocols. This integration promotes efficiency and expedites the overall service delivery, ensuring a more efficient and responsive healthcare administration system.

Prior authorization (PA) is a method used by payers (e.g., healthcare insurance companies) to confirm if a service (e.g., medical service) is medically necessary for a patient. For example, before the service is rendered, a healthcare provider (e.g., healthcare professionals such as medical doctors) or patients must obtain PA from the payers, or the claim may be denied. Payers may also outsource the PA review process to a third-party utilization management organization (UMO). PAs are primarily used by payers to manage healthcare utilization and control costs. As mentioned, PA must be obtained before a service is rendered, or the claim may be denied, making PAs the leading cause of provider burden and denials.

Such process of authorizing the services (or PA) is a complex, highly manual, and can vary greatly by payer and service requested. For example, each payer has their unique set of rules for determining which services require authorization and how the authorization must be obtained. Over 80% of authorizations are processed through a payer's web portal or fax machine, which causes incapability or inability to normalize or standardize formatting across authorization requests and is accordingly inefficient (e.g., in terms of data sharing and communicating using unstandardized data sharing procedures, inconsistency in data format, timely inefficient to manually visit different payer's web portals, may be disorganized, causes portal fatigue, etc.).

Implementations according to this disclosure provide enhanced transmission and automation of medical data, standardization of such data transmission procedure and data format, connectivity, and/or single access point for processing authorizations (or PAs) between multiple payers and clients (e.g., healthcare professionals, individuals, end-users, etc.). Clearinghouse services and application programming interfaces (APIs) of the third-party vendors (e.g., payers, UMOs) may be used in accordance with implementations of this disclosure to communicatively connect multiple payers in the single access point. Insurance can be checked automatically when an order (e.g., healthcare service order) is created. Processing authorizations on the order can be facilitated through automation of such authorization processes by directly communicating (e.g., through use of clearinghouse services, third-party vendors API, open-source API, scraper script, etc.) with third-party vendors, defining payer rules on backend server application, utilizing electronic data interchange (EDI) standard, and/or utilizing scraper to find and parse necessary information (e.g., desired authorization requirement information) on the web. For example, the backend server application may utilize stored list of medical procedure codes and/or diagnosis codes to perform authorization requirement determination. For example, the backend server application may be combined with established direct connection (e.g., third-party integrations) with entities mentioned above and the scraper to perform authorization requirement determination. For example, the backend server application or a server that is in data communication with the backend server application may store payer rules (e.g., payer identifiers, payer APIs, authorization requirement information, other relevant information that can be obtained and stored, etc.) and utilize such information to automate authorization procurement process and/or connect with entities mentioned above to obtain relevant data in automating authorization procurement process. For example, the scraper script and the scraper in medical service provider's device or the server application may be used independently and/or to supplement in automating the authorization procurement process. For example, the backend server application may be configured to execute different combinations of utilizing the stored procedure codes, third-party integrations, and the scraper in different sequences with regards to creating, analyzing and processing the medical service order, automating data entry, determining the authorization requirement, submitting the authorization request to the third-party vendor, and monitoring the status of the authorization request. For example, the server application may implement specific formatting rules and/or transformation rules such that information that is obtained through the third-party integrations or through other outside sources can be converted into a standardized data format. For example, the server application may utilize SQL (Structured Query Language) server database to store and pull structured data in a tabular and standardized data format.

Reference will now be made in detail to certain illustrative implementations, examples of which are illustrated in the accompanying drawings. Wherever possible, the same reference numbers will be used throughout the drawings to refer to the same or like items.

FIG. 1 is a block diagram of an example architecture of a system 100 for automating prior authorizations in accordance with implementations of this disclosure. The system 100 may include a client device 120 connected to or in communication with (collectively "connected to") a clearinghouse service 130, and one or more third-party vendor 140 via a network 140. In an implementation, the system 100 may execute method and techniques described in FIGS. 5-8. The connections between the client device 120, the clearinghouse service 130, and the one or more third-party vendor 140 may be established for authorization (e.g., PA) techniques supplemented herein. In some implementations, such connections may be established via the network 140, and API of different devices and/or entities including the client device 120, the clearinghouse service 130, and/or the one or more third-party vendor 140. The system 100 and the components therein may include other elements which may be desirable or necessary to implement the devices, systems, compositions, and methods described herein.

The client device 120 may be a computing device (such as a computing device 200 shown in FIG. 2) including an end-user device, information appliances, mobile computers, laptops, handheld computers, personal media devices, smartphones, notebooks, notepads, and tablets, cloud-based platform, distributed computing platform, and the like. The client device 120 may include or run a software or an application for processing authorizations (or PAs related to medical service orders) in accordance with implementations of this disclosure. The clients (e.g., healthcare professionals, individuals, end-users, etc.) may users of the client device 120.

The one or more third-party vendor 140 may include a payer (e.g., healthcare insurance companies), third-party UMO utilized by or associated with the payer. Moreover, the one or more third-party vendor 140 may include computing device, cloud-based platform, distributed computing platform, website, a software, an application, API, and the like of the payer and the UMO. Although not illustrated in FIG. 1, UMO may be in communication or connected to the healthcare insurance companies via network such as the network 150.

The clearinghouse service 130 may be a service that processes health information and carries out billing transactions between healthcare providers and insurance companies (e.g., third-party vendor 140). For example, the clearinghouse service 130 may serve as an intermediary that takes in data from the clients (e.g., healthcare providers, individuals, end-users, etc.), standardizes the data format to be compliant with health insurance requirements, and forward the information to the relevant insurance companies (e.g., 140 third-party vendor) for processing. For example, the clearinghouse service 130 may serve as electronic stations or hubs that allow the clients to transmit service orders (e.g., claims) and relevant information to insurance companies. Other aspects of conventional clearinghouse service may be applied and integrated in accordance with the implementations of this disclosure.

Moreover, the clearinghouse service 130, the client device 120, and the third-party vendor 140 may also utilize Electronic Data Interchange (EDI), which is a set of standards for structuring information that is electronically exchanged between and within the clearinghouse service 130, client device 120, and the third-party vendor 140, businesses, organizations, government entities, and other groups. For example, the clearinghouse service 130, the client device 120, and the third-party vendor 140 may utilize specific EDI transaction set within X12 standard (e.g., X12 278) to exchange data between (or among) each other. Different types of transaction sets may be used depending on different types and/or needs of the clearinghouse service 130, the client device 120, the third-party vendor 140, businesses, and the like. The network 150 may be and may include the Internet, an intranet, a local area network (LAN), a wide area network (WAN), a public network, a private network, network gateway, a cellular network, a Wi-Fi-based network, a telephone network, a landline network, public switched telephone network (PSTN), a wireless network, a wired network, a private branch exchange (PBX), an Integrated Services Digital Network (ISDN), a IP Multimedia Services (IMS) network, a Voice over Internet Protocol (VoIP) network, an IP network, cable, satellite, hybrid coaxial systems, fiberoptic systems, 5G, autonomous vehicle parking, and like including any combinations thereof. In an implementation, the network 150 may contain one or more servers, network elements or devices, and the like.

Figure 2:
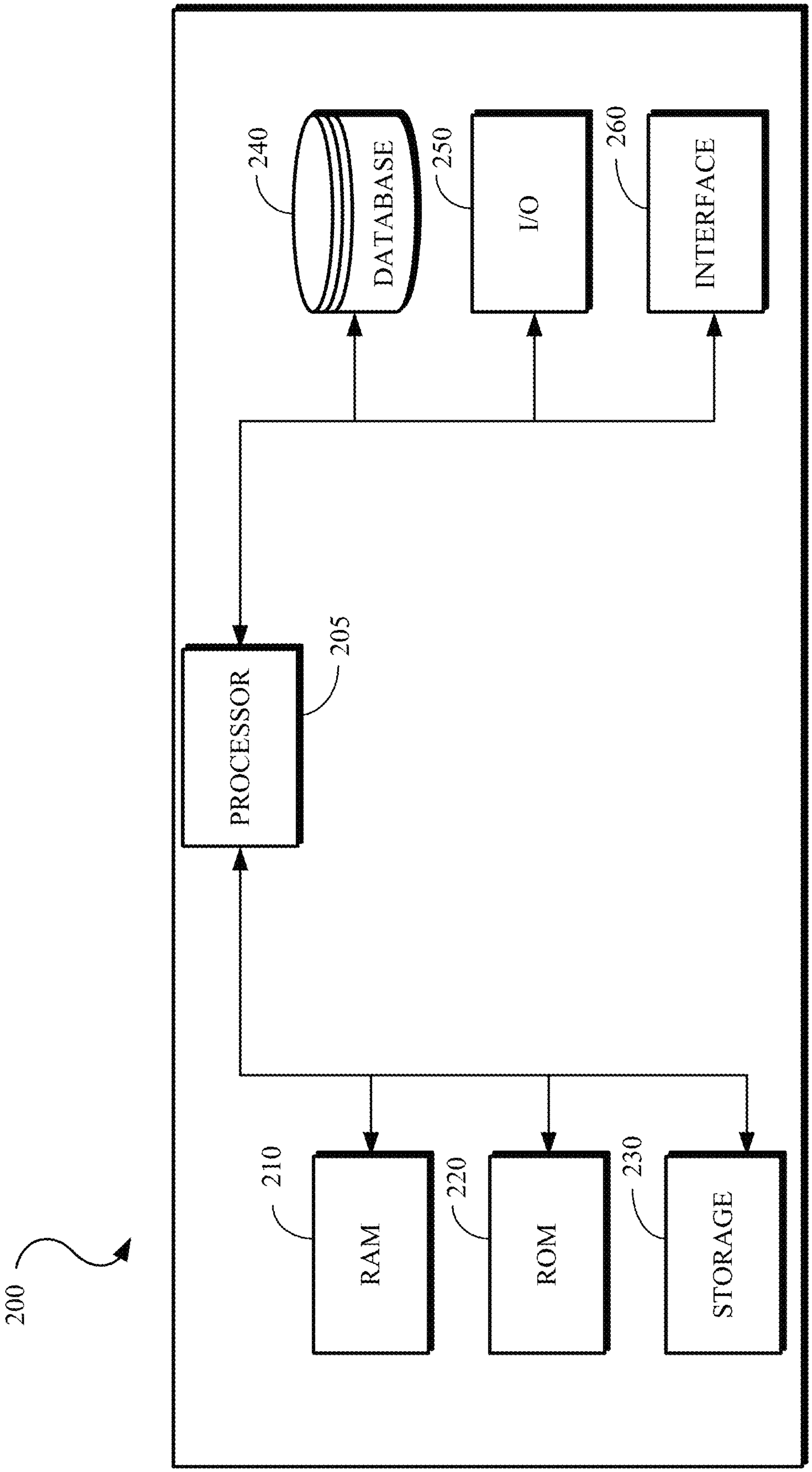
FIG. 2 depicts an illustrative processor-based, computing device.

FIG. 2 depicts an illustrative processor-based, computing device 200. The computing device 200 can implement automated prior authorizations technique, run an application or software related to automated prior authorizations technique. The computing device 200 is representative of the type of computing device that may be present in or used in conjunction with at least some aspects of the client device 120 of FIG. 1 and/or other devices at least partially implementing functionality or techniques described with respect to the system 100 of FIG. 1, or any other device that includes electronic circuitry. The computing device 200 is illustrative only and does not exclude the possibility of another processor- or controller-based system being used in or with any of the aforementioned aspects of the client device 120.

In one aspect, the computing device 200 may include one or more hardware and/or software components configured to execute software programs, such as software for obtaining, storing, processing, and analyzing signals, data, or both. For example, the computing device 200 may include one or more hardware components such as, for example, a processor 205, a random-access memory (RAM) 210, a read-only memory (ROM) 220, a storage 230, a database 240, one or more input/output (I/O) modules 250, and an interface 260. Alternatively, and/or additionally, the computing device 200 may include one or more software components such as, for example, a computer-readable medium including computer-executable instructions for performing techniques or implement functions of tools consistent for automating prior authorizations. It is contemplated that one or more of the hardware components listed above may be implemented using software. For example, the storage 230 may include a software partition associated with one or more other hardware components of the computing device 200. The computing device 200 may include additional, fewer, and/or different components than those listed above. It is understood that the components listed above are illustrative only and not intended to be limiting or exclude suitable alternatives or additional components.

The processor 205 may include one or more processors, each configured to execute instructions and process data to perform one or more functions associated with the computing device 200. The term "processor," as generally used herein, refers to any logic processing unit, such as one or more central processing units (CPUs), digital signal processors (DSPs), application specific integrated circuits (ASICs), field programmable gate arrays (FPGAs), and similar devices. As illustrated in FIG. 2, the processor 205 may be communicatively coupled to the RAM 210, the ROM 220, the storage 230, the database 240, the I/O module 250, and the interface 260. The processor 205 may be configured to execute sequences of computer program instructions to perform various processes (e.g., techniques), such as those described herein for automating prior authorizations. The computer program instructions may be loaded into the RAM 210 for execution by the processor 205.

The RAM 210 and the ROM 220 may each include one or more devices for storing information associated with an operation of the computing device 200 and/or the processor 205. For example, the ROM 220 may include a memory device configured to access and store information associated with the computing device 300, including information for identifying, initializing, and monitoring the operation of one or more components and subsystems of the computing device 200. The RAM 210 may include a memory device for storing data associated with one or more operations of the processor 205. For example, the ROM 220 may load instructions into the RAM 210 for execution by the processor 205.

The storage 230 may include any type of storage device configured to store information that the processor 205 may use to perform processes consistent with the disclosed implementations. The database 240 may include one or more software and/or hardware components that cooperate to store, organize, sort, filter, and/or arrange data used by the computing device 200 and/or the processor 205. For example, the database 240 may include end-user profile information, historical activity and end-user specific information, predetermined menu/display options, and other end-user related data. Alternatively, the database 240 may store additional and/or different information. The database 240 can be used to store admin data, patient data, order-related data, authorization-related data and/or other data used or generated in accordance with implementations of this disclosure.

The I/O module 250 may include one or more components configured to communicate information with a user associated with the computing device 200. For example, the I/O module 250 may comprise one or more buttons, switches, or touchscreens to allow a user to input parameters associated with the computing device 200. The I/O module 250 may also include a display including a graphical user interface (GUI) and/or one or more light sources for outputting information to the user. The I/O module 250 may also include one or more communication channels for connecting the computing device 200 to one or more secondary or peripheral devices such as, for example, a desktop computer, a laptop, a tablet, a smart phone, a flash drive, or a printer, to allow a user to input data to or output data from the computing device 200.

The Interface 260 may include one or more components configured to transmit and receive data via a communication network, such as the Internet, a local area network, a workstation peer-to-peer network, a direct link network, a wireless network, or any other suitable communication channel. For example, the interface 260 may include one or more modulators, demodulators, multiplexers, demultiplexers, network communication devices, wireless devices, antennas, modems, and any other type of device configured to enable data communication via a communication network.

Figure 3:
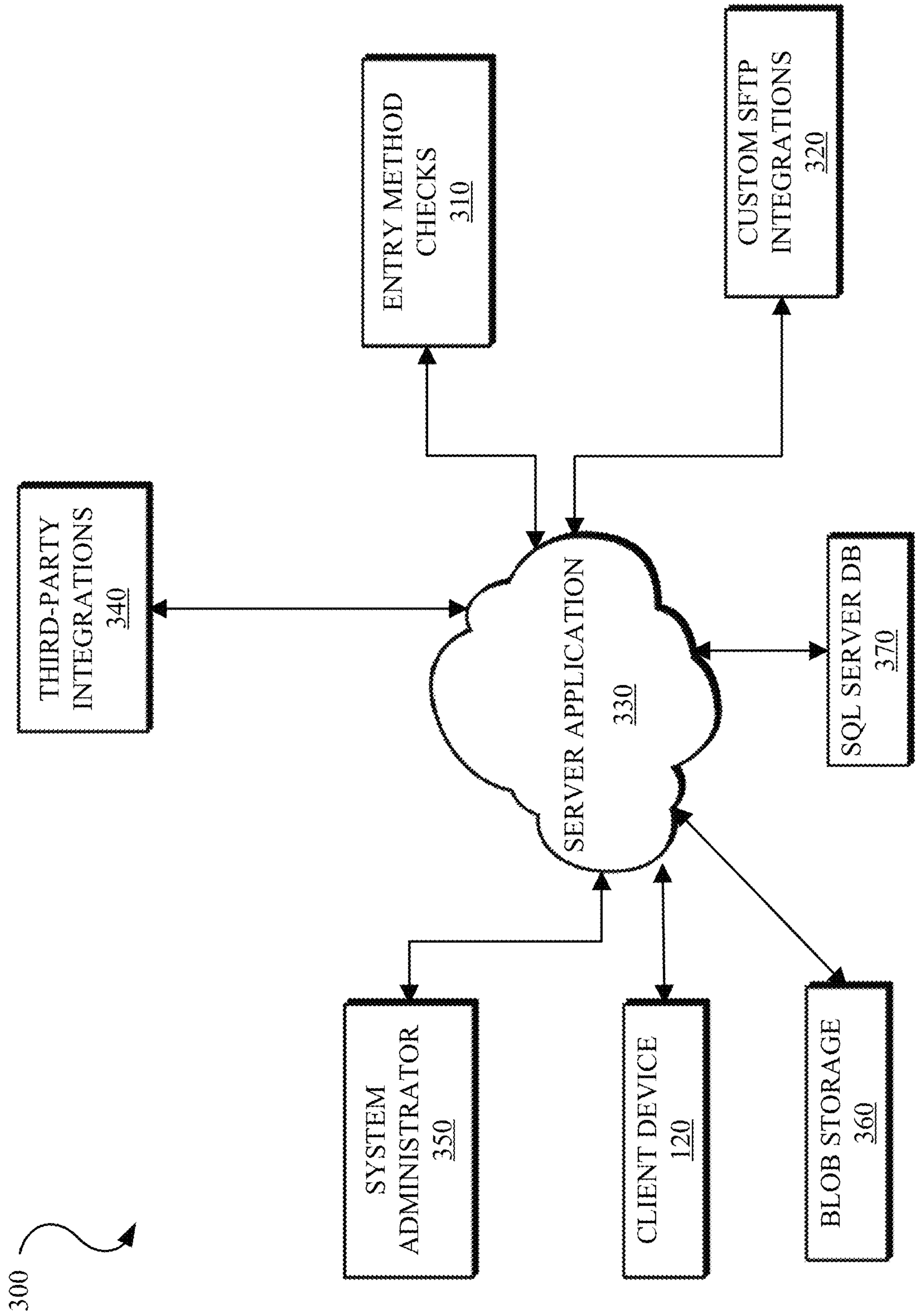
FIG. 3 is a block diagram of an example architecture of a system for automating prior authorizations in accordance with implementations of this disclosure.

FIG. 3 is a block diagram of an example architecture of a system 300 for automating prior authorizations in accordance with implementations of this disclosure. The system 300 may include a server application 330 connected to or in communication with (collectively "connected to") the client device 120, entry method checks 310, custom SFTP integrations 320, third-party integrations 340, a system administrator 350, a blob storage 360, a SQL server database 370 via a network such as the network 140. In an implementation, the system 300 may execute the techniques described in FIGS. 5-8. Such connections may be established for authorization (e.g., PA) techniques, and other supportive and functional steps supplemented herein. The system 300 and the components therein may include other elements which may be desirable or necessary to implement the devices, systems, compositions, and methods described herein.

The server application 330 may be or include a backend of a software application, and/or a backend server that communicates (e.g., in data communication) with the software application for processing authorizations (or PAs) between the one or more third-party vendor 140 and the clients (e.g., healthcare professionals, individuals, end-users, etc.) who are using or accessing the client device 120. Moreover, the server application 330 may include its own processor configured to execute instructions and cooperate with the client device 120 in executing instructions. Moreover, the server application 330 or the backend server may include or communicate with a data store or a storage space (e.g., a server of the backend server, any cloud server of the system). Throughout this disclosure, when it is mentioned that the server application 330, the backend server, or the backend of the software application stores data, it may be referring to the data store or the storage space in any feasible manner. The server application 330 may communicate with (e.g., connected to) third-parties of the third-party integrations 340 including the electronic medical record (EMR) provider (or EMR system), clearinghouse services, the third-party vendor (e.g., healthcare insurance companies, UMOs), and other relevant third parties. For example, the server application 330 may act as a single access point for accessing different information (e.g., rules, policies, information of the healthcare insurance companies) from many different third-parties of the third-party integrations 340. The server application 330 or the software application may utilize and be viewed in conjunction with the system 100, the computing device 200, the system 300, a method 500, technique 600, 700, 800 in accordance with implementations of this disclosure.

The third-party integrations 340 may be or indicate integrations of the third-parties including the EMR provider (or EMR system), clearinghouse services, the third-party vendor (e.g., healthcare insurance companies, UMOs), and other third parties that may be connected to or in data communication with the server application 330. For example, the server application 330 may be connected to or communicate with the third-party integrations through API. For example, the API may be the APIs of the third-parties, or open-source APIs that may communicate with the APIs of the third-parties.

The entry method checks 310 may determine where an authorization request (e.g., PA) may be sent among the third-parties of the third-party integrations 340. For example, the entry method checks 310 may communicate with components of the system 300 and identify where the authorization request may be sent. For example, after determining requirements of the authorization or whether authorization is required on created order, it may process the information in the requirements of the authorization and determine where (which third-party of the third-party integrations 340) to submit the prior authorization request.

Figure 5:
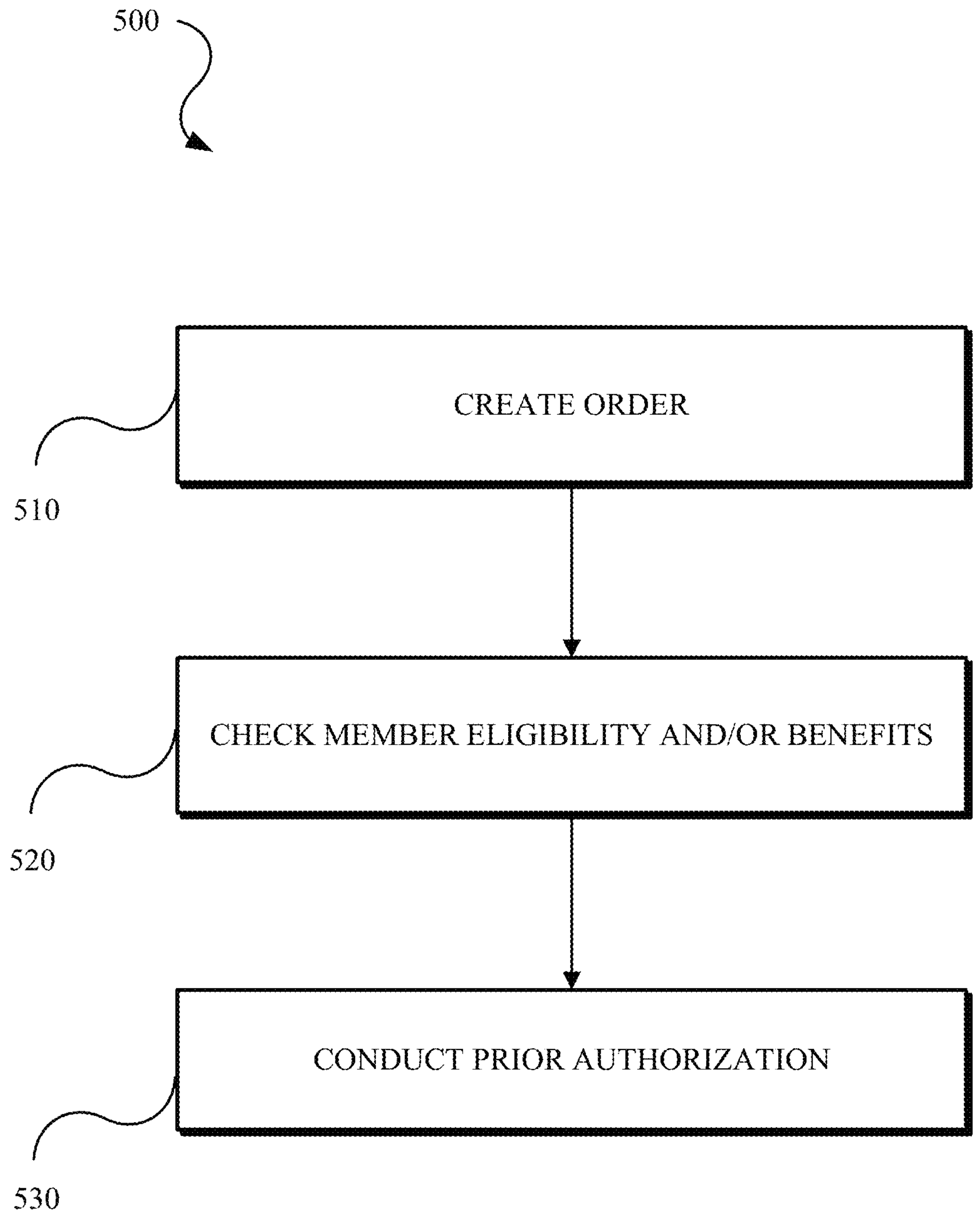
FIG. 5 is a flowchart of a method for automating prior authorizations in accordance with implementations of this disclosure.
Figure 6:
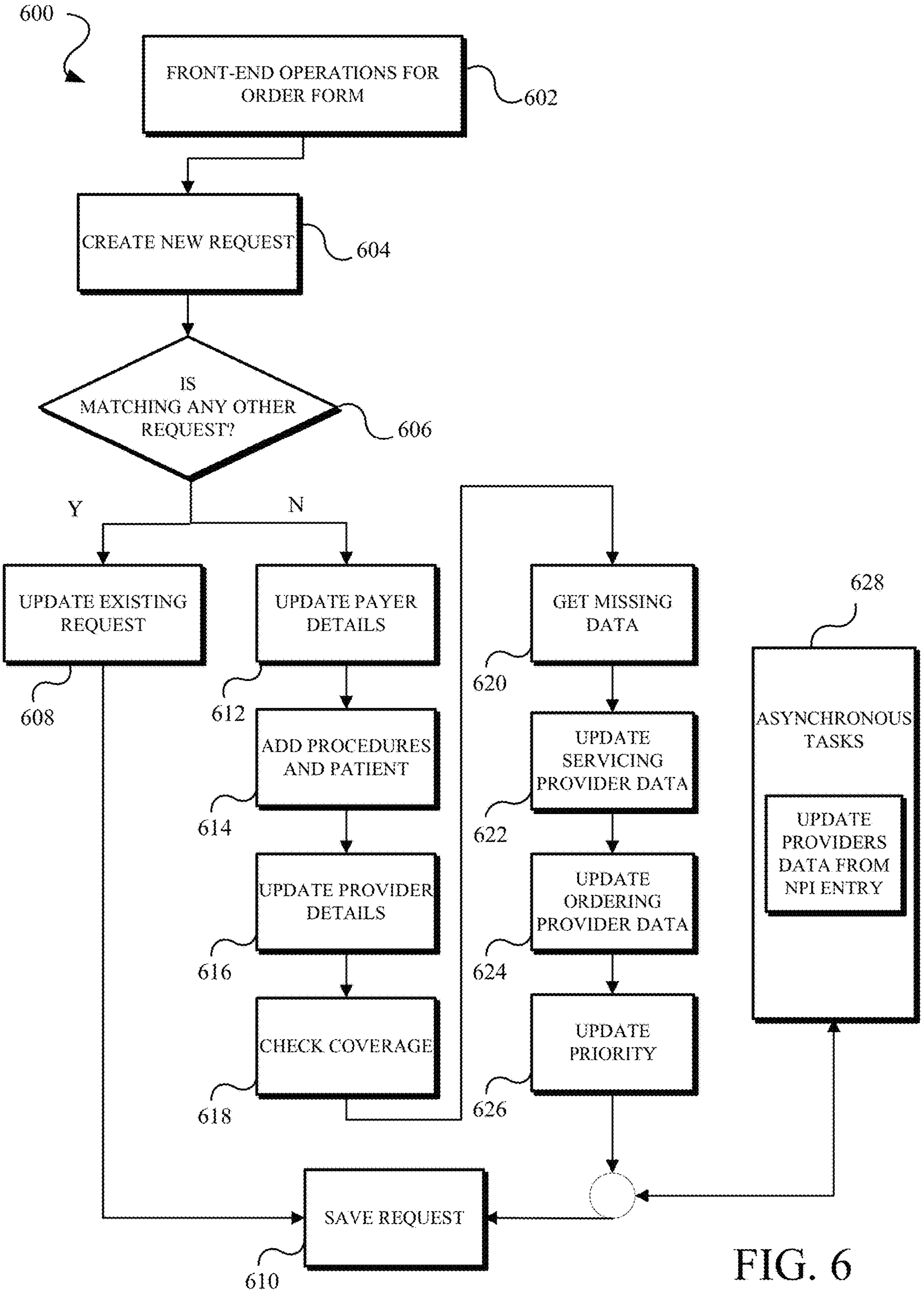
FIG. 6 is a flowchart of an example of a technique for creating and processing healthcare service orders in accordance with implementations of this disclosure.

As described above, the client device 120 may include or run the software or the application (e.g., software application). The clients of client device 120 may interact with the client device 120 with regards to a front-end of the software or the application. For example, the client device 120 may be used to create an order or request for the order (e.g., medical service order, healthcare service prescribed by the medical service provider). For example, the order creation can be automated through the server application 330, or conducted through cooperation of both the client device 120 and the server application 330. Detailed description of the order creation is shown in the discussion of FIGS. 5 and 6.

Moreover, the client device 120 may run a scraper (e.g., web scraper) based on a scraper script that may include code or instructions that may load and navigate particular web portals (e.g., website, web page) of the third-parties of the third-party integrations 340 or the pre-determined web portals that are associated with information (or data) in determining whether prior authorization is required on the order, and find and extract specific data related to the authorization. For example, the scraper may check a request status of the prior authorization, obtain existing requests from UMO portals that are not yet added to the database or server (e.g., database of the client device 120 or the computing device 200, a server of the server application 330, any cloud server of the system 300). For example, the scraper may detect errors when filling out forms (e.g., authorization request form, order form) and/or creating the order. Moreover, if some way to find the authorization request fails, the scraper script may have secondary code or instructions to direct the scraper to do it another way (e.g., using different search word, broadening search scope). For example, the scraper may detect that a user (e.g., the client) does not have access to the specific information or request, or specific information or request does not exist.

The scraper may be operated in "headless mode," which makes the browser run in the background and is invisible to the user (e.g., the client). The scraper may also be operated in "full mode," which makes the browser visible, as if it were a browser opened by the user (e.g., the client). For example, when the scraper is operating in the full mode, the scraper may display appropriate hints in an overlay on the webpage such that the user recognizes if an action is currently being performed by the script or if the user needs to perform certain actions. For example, when the scraper is operating in the full mode, the scraper may wait for a specific element and then fill in specific fields or may display a hint to the user and wait for user's action. For example, when the scraper is operating in the full mode, the scraper may detect the summary page and obtain key data (e.g., authorization status, payer notes, authorization ID, cases ID). For example, the scraper may log into a web portal and detect key elements, fill in data in an order form and/or an authorization request form if necessary, and proceeds until specific search inquiry or requirement that activated the scraper is met. The scraper can scrape the details which are transmitted over the network to the server application and can be automatically entered into specific fields or form (e.g., order form, authorization request form). For example, the scraper script may include steps or instructions to transmit HTTP requests (with login credentials) to a server of the website, simulating a user log in action, use a parsing library to navigate document object model of the website to detect key elements and fill in data, include conditional statements in script to control when to initiate and/or stop, identify necessary elements on the webpage and extract relevant data, and transmit data to the server application. Moreover, for example, extracted data from the website may be typically stored in a structured format like JSON, CSV, etc, and the scraper script may use a database driver or Object-Relational Mapping (ORM) tool to connect to target database or storage location (e.g., SQL server database 370). For example, extracted data may be prepared in a format suitable for insertion into the storage location, which may involve mapping the data to correct table and columns, and converting the data to the correct types, and the data may be inserted into the storage location.

In some implementations, the scraper script may be implemented in the server application 330 or the front-end of the software application that is running on the client device 120, and the client device 120 may cooperate with the front-end or the server application 330 to load the scraper and execute instructions associated with the scraper script. In some implementations, the server application 330 may run and control the scraper in the client device 120. For example, the scraper script may be on the server application 330 side in controlling the execution of the client device 120 side scraper, as this may be useful for distributing the scraping workload while maintaining control over the scraping process. For example, the server application 330 may transmit commands or instructions in when to start or stop scraping, or to change the target of the scraping, and so on.

In some implementations, the scraper script may run on the client device 120 that has established communication mechanisms with the server application 330 such that the server application can trigger and/or activate scraper script, e.g., through web sockets, push notifications, API calls, etc.

In some implementations, depending on a type of website or web portal where the scraping may be performed, the scraper may be operated in either the headless mode, the full mode, or the combination of both. For example, each mode may have advantages and considerations based on the type of the web portal where the scraping may be performed. For example, the scraper script may direct the scraper to automatically browse a web portal of the third-party vendor and fill out a first portion of necessary information for the prior authorization request in a headless mode or full mode, and after the portion of the necessary information is filled, direct a user to fill out a second portion of the necessary information for the prior authorization request in a full mode. For example, when some tasks are needed to be assisted by the user, then the scraper may run in the full mode. For example, when the tasks need a discretion of the user or include information that cannot be entered by the headless mode completely or in accurate manner, or require further confirmation by the user, the scraper may run in the full mode to require assistance from the user. For example, the scraper script may display appropriate hints in the overlay on the webpage, so that the user knows if the action is currently being performed by the script or if the user should take an action.

The system administrator 350 may have access to an admin panel, and manage users and accesses, the third-party integrations 340, data (e.g., data table) that includes information related to creating, storing, transmitting, or updating the order (e.g., procedure codes, patient information, etc.), and other necessary administrative and functional information or communicated information relating to running the software, creating the order, checking member eligibility and/or benefits, and conducting prior authorization.

The custom SFTP (a Secure File Transfer Protocol) integrations 320 may indicate or be integrations with healthcare providers' SFTP servers. The custom SFTP integrations 320 may be used as a system or method for healthcare providers to create orders and send files, such as orders in HL7 or CSV formats, to other systems or organizations. This may involve sending these files to the third-parties of the third-party integrations 340 and any other entity that needs to receive the data. The custom SFTP (a Secure File Transfer Protocol) integrations 320 may also be or include a SFTP server (e.g., cloud server) which may take a form of a file share repository where files can be deposited and retrieved. In some implementations, some (not all) orders can be created utilizing the custom SFTP integrations 320. In some implementations created orders (regardless of whether the orders were created using the custom SFTP integrations 320) may utilize the custom SFTP integrations 320 to send files to appropriate destinations or store them in the SFTP server. The server application 330 or the client device that runs the application may store and/or pull data from the custom SFTP integrations 320.

The blob storage 360 may be a cloud server which allows storage of unstructured data that can be accessed via Hypertext Transfer Protocol (HTTP) or Hypertext Transfer Protocol Secure (HTTPS). The blob storage 360 may store files such as order documents, and any documents related to the order. For example, the blob storage 360 may store screenshot of authorization request, pdf document of eligibility and/or benefits information, EMR related document, attachment documents of the order, files received from a EMR system, the third-party integrations (e.g., EMR provider, EMR system, third-party vendor, the clearinghouse services, etc.) and other order-related and authorization-related documents and attachments. Moreover, Microsoft Azure, Google Cloud, and Amazon Web Services (AWS) are some examples of cloud providers that offer blob storage services. The server application 330 or the client device that runs the application may store and/or pull data from the blob storage 360.

The SQL server database 370 may be a cloud server which may store structured data in a tabular format. The SQL server database 370 may store order information and other order-related information in a data model and standardize data into standardized data format. For example, order information and other order-relation information, which include information regarding patient's eligibility and/or benefits, order, authorization status (e.g., PA status), authorization requirement, other information received from the third-party vendor and/or clearinghouse services, may be mapped into the data model such that the data representing such information may be standardized into standardized data format. For example, the data can be stored in the JSON format, or any other feasible standardized format. The server application 330 or the client device that runs the application may store and/or pull data from the SQL server database 370. For example, as described above, extracted data obtained from outside sources (e.g., website, third-party integrations) may be stored in the structured format. In an example, the scraper script may use a database driver or Object-Relational Mapping (ORM) tool to connect to the SQL server database 370 and extracted data may be prepared in a format suitable for insertion into the storage location, which may involve mapping the data to correct table and columns, and converting the data to the correct types, and the data may be inserted into the SQL server database 370. In an example, the server application may parse received data (e.g., response from API) into standardized format for processing and/or storing into the SQL server database 370 in a similar manner described with respect to the scraper script.

As initially described, PA must be obtained before a service is rendered, or the claim may be denied, making PAs the leading cause of provider burden and denials.

Figure 4:
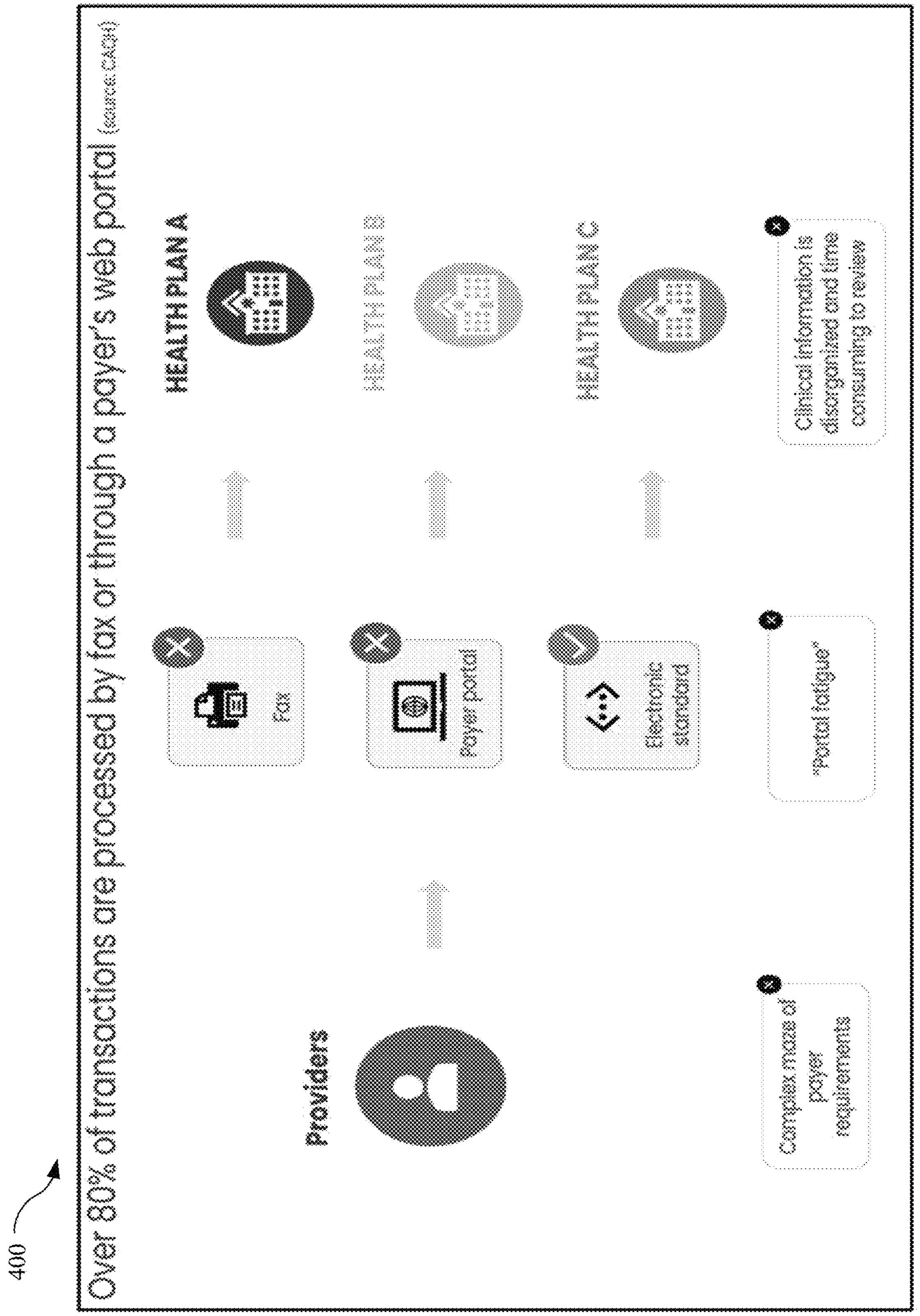
FIG. 4 depicts an example illustrating some of the issues caused by conventional system for prior authorizations.

Such process of authorizing the services (or PA) is a complex, highly manual, and can vary greatly by payer and service requested. For example, each payer has their unique set of rules for determining which services require authorization and how the authorization must be obtained. Over 80% of authorizations are processed through a payer's web portal or fax machine, which causes incapability or inability to normalize or standardize formatting across authorization requests and is accordingly inefficient (e.g., in terms of data sharing and communicating using unstandardized data sharing procedures, inconsistency in data format, timely inefficient to manually visit different payer's web portals, may be disorganized, causes portal fatigue), as shown in FIG. 4. FIG. 4 depicts an example illustration 400 depicting one of the issues caused by conventional system for prior authorizations. As the FIG. 4 illustrates, over 80% of transactions are processed by fax or through a payer's web portal. Further, complexity of payer requirements and disorganized clinical information among different payers and health plans attribute to inefficiency and administrative costs.

Implementations according to this disclosure provide connectivity and single access point for processing authorizations (or PAs) between multiple payers and clients (e.g., healthcare professionals, individuals, end-users, etc.) to address issues described above. Clearinghouse services and APIs of the third-party vendors (e.g., payers, UMOs) may be used in accordance with implementations of this disclosure to communicatively connect multiple payers in the single access point. Insurance can be checked automatically when an order (e.g., healthcare service order) is created. Processing authorizations on the order can be facilitated through automation of such authorization processes by directly communicating (e.g., through use of clearinghouse services, third-party vendors API, open-source API, scraper script, etc.) with third-party vendors, defining payer rules on backend server application, utilizing electronic data interchange (EDI) standard, and/or utilizing scraper to find and parse necessary information (e.g., desired authorization requirement information) on the web.

FIG. 5 is a flowchart of a method 500 for automating prior authorizations in accordance with implementations of this disclosure. The method 500 may be implemented by processor-based device, such as the client device 120, the computing device 200, and/or the server (e.g., the backend server such as the server application 330, any cloud server described of the system 300). The computing device 200 is representative of the type of computing device that may be present in or used in conjunction with at least some aspects of the client device 120, the server or any other device that includes electronic circuitry.

Further, the method 500 may implement, be implemented by, or in conjunction with the system 100, the system 300, and in accordance with implementations of this disclosure.

At 510, the method 500 may create an order (e.g., healthcare service order). For example, the order may be created by entering information including at least a name of a patient, member, or end-user, a date of birth, identification code (e.g., member ID pertinent to payer), payer (e.g., healthcare insurance company) identification information (e.g., title or name of the company). For example, request for the order may be created by utilizing front-end of a software application, which may involve client interaction (e.g., interaction from healthcare professionals, individuals, end-users, etc.) for input on the client device (such as the device 120, the computing device 200, etc.). For example, request for the order can be supplemented by automated entry from backend of the software application (e.g., server application 330). Moreover, after request for the order is created, the order may be created from the back-end of the software application.

In some implementations, the front end and the back end of the software application may be combined to fill (e.g., enter), create, or complete the order. For example, the front end may be utilized for entering portion of data or portion of information pertinent to information described in the preceding paragraph, described in below Table 1, FIG. 6, and/or other pertinent order information in accordance with implementations of this disclosure, and the back end may be utilized for entering rest of the data or information. For example, the backend (e.g., server application) may complete the order with additional data representing service type (based on medical procedure) and/or healthcare provider information such as tax ID or national provider identification number based on the organization's configuration. With these data, the backend may also communicate with clearinghouse services (e.g., clearinghouse partners) by sending request to and receiving response from the clearinghouse services through e.g., API of the clearinghouse services. Such communication of sending request and receiving response may be programmed or automated by the method 500 or the backend of the software application that utilizes the method 500. Upon receiving the response from the clearinghouse services or the API of the clearinghouse services, the response may be automatically stored or entered in the order, and/or available to the client. Moreover, the backend of the software application (e.g., server application) or the client device that runs the software application may utilize a scraper (with automated browser and web scraping function) to find and automate (or assist in automating) entries for the order. For example, when there is an error in communicating with the clearinghouse services or when it is not feasible to use the clearinghouse services or when additional information that cannot be obtained through the clearinghouse services is needed, the scraper may be utilized to find and automate (or assist in automating) unfilled entries for the order. As such, the order may be created by entering the information as described above and additional information such as information described in below Table 1, FIG. 6, and/or other pertinent order information in accordance with implementations of this disclosure.

TABLE 1

| | |
|---|---|
| Member information | Includes patient demographic and insurance information |
| Order information | Includes services ordered by the provider, including patient diagnosis, place of service, and other related information |
| Authorization information | Includes information about authorization requirements, authorization status, and authorization effective/expiration dates, which is the date of service range in which the payer approves for requested services |
| Ordering provider | Provider who ordered the service |
| Servicing provider | Provider who will render the service or Facility where the service will get rendered |

Moreover, the order may be created in any feasible way according to implementations disclosed in a technique 600 of FIG. 6.

At 520, the method 500 may check member eligibility and/or benefits (e.g., of patient's insurance coverage or information related to one or more healthcare insurance companies, which pertain to the created order or the information in the order). For example, the member eligibility and/or benefits can be determined through third party integrations (such as the third-party integrations 340).

In some implementations, after or responsive to the creation of the order, the method 500 may utilize EMR data from the client device, a EMR server (server that stores the EMR data that is communicatively connected to the client device), or EMR provider that provides EMR data to contact (e.g., automatically contact) the third-party vendor (e.g., via third-party vendor API) to check member eligibility and/or benefits. For example, the software application running on the client device that implements the method 500 may automatically communicate (e.g., request and receive response) with the third-party vendor (e.g., through third-party vendor API) to obtain data or information pertaining to member eligibility and/or benefits based on the EMR data. For example, EMR data may be conventional EMR data which may represent comprehensive patient information including insurance details. For example, when the patients visit the client (e.g., healthcare provider), their insurance information may be collected and stored in EMR systems or application through client device, the EMR server that is communicatively connected to the client device, and/or by the EMR provider.

In some implementations, the method 500 may utilize connections through clearinghouse services (e.g., clearinghouse services API) to automatically check member eligibility and/or benefits. For example, the clearinghouse services may be integrated with the EMR systems to verify the patient's insurance coverage or information related to one or more healthcare insurance companies, which pertain to the created order or the information in the order. That is, direct communication (e.g., send request and receive response) between the client device (or software application that implements the method 500) and the clearinghouse services may be used to automatically check member eligibility and/or benefits.

In some implementations, the scraper may be utilized (e.g., by the client device that runs the software application, by the software application, by the backend). For example, when there is an error in communicating with the clearinghouse services or third-party vendors, or when it is not feasible to use the clearinghouse services or directly communicate with the third-party vendor, or when additional information that cannot be obtained through the clearinghouse services is needed, the scraper may be utilized to check for eligibility and benefits, and/or automate information input or notification regarding the search result of the eligibility and benefits. For example, when the healthcare insurance company is not a clearinghouse partner or information must be checked through the third-party UMO (and assuming that direct communication with UMO is not feasible), the scraper may be utilized to browse web portals (e.g., UMO portals, other web portals) to check for eligibility and benefits, and utilize obtained information or data to automate entry and/or transmittal of notification regarding the search result of the eligibility and benefits.

At 530, the method 500 may conduct a prior authorization of the order. Conducting the prior authorization may include determining whether or not prior authorization is required on the order, submitting a prior authorization request to the third-party vendor, and monitoring a status of the prior authorization request. These steps are further explained in a discussion of a technique 700 of FIG. 7. As such, step 530 may be implemented in any feasible way according to the technique 700 and other implementations of this disclosure.

FIG. 6 is a flowchart of an example of a technique 600 for creating and processing healthcare service orders in accordance with implementations of this disclosure. The technique 600 may be implemented by processor-based device, such as the client device 120, the computing device 200, and/or a server (e.g., the backend server such as the server application 330, any cloud server described of the system 300). The computing device 200 is representative of the type of computing device that may be present in or used in conjunction with at least some aspects of the client device 120, the server, or any other device that includes electronic circuitry.

Further, the technique 600 may implement, be implemented by, or in conjunction with the system 100, the system 300, and in accordance with implementations of this disclosure.

At 602, the technique 600 may involve front-end operations for conducting preliminary steps for putting in a request for creation of an order or initiating the request of the order. For example, a user (e.g., end-user, medical service provider, medical professionals, administrative staff) may open a new request form, perform a member search (e.g., patient search), enter procedure codes, enter diagnosis codes, and select ordering provider and servicing provider. For example, member data, the procedure codes, the diagnosis codes, ordering provider and servicing provider data may be stored in the server (e.g., the backend server such as the server application 330, any cloud server described of the system 300), and the user may lookup these data in performing front-end operations. Even though these lookup and preliminary steps are described with respect to front-end operations, they are not limited to being performed solely by the front-end operations, and any of these steps may be performed independently or through assistance via back-end operations.

Rest of steps (604-628) of the technique 600 may involve back-end operations, which can be automated (e.g., performed automatically without user input).

At 604, the technique 600 may create a new request of the order.

At 606, it can be determined whether the new request matches any other existing request. In some implementations, the technique 600 may search the server to determine if there are any other existing request that matches the new request. In some implementations, the technique 600 may utilize third-party integrations (such as the third-party integrations 340) and/or scraper (such as the scraper discussed in FIG. 3) to search whether there is an existing request that matches the new request. For example, the scraper may be used to search for, and add existing request from UMO portals that are not yet added to the server.

When the new request matches the existing request, then the request may be updated at step 608, and saved to the server at step 610.

When the new request does not match the existing request, then the payer details may be updated at step 612. For example, payer assignment (to the patient) and payer details may be updated based on insurance plan identifier or health plan identifier.

At 614, procedure and patient information may be added (e.g., entered) or updated.

At 616, servicing provider and/or ordering provider details may be updated.

At 618, insurance coverage may be checked. For example, the technique 600 may first check if the payer is entered or if necessary payer information for checking insurance coverage is entered, and then check the insurance coverage details. If the payer is not entered or if necessary payer information is not entered, then the technique 600 may utilize the third-party integrations to look-up and/or enter coverage information from the third-parties. For example, the technique 600 may connect to the clearinghouse services (e.g., through clearinghouse services API) and obtain coverage details.

At 620, the technique 600 may check which data in the request is missing. For example, whether procedure code, diagnosis code, ordering provider NPI, servicing provider NPI, and/or coverage errors are properly entered can be checked. If there is an error or missing data, then a proper flag is saved in the request.

At 622 and 624, the technique 600 may update servicing provider data and ordering provider data. For example, the technique 600 may check whether the servicing provider data and the ordering provider data exist in the server based on identifiers such as NPI (National Provider Identifier). If it cannot be properly checked and updated, then flag indicating that corresponding data must be updated from the NPI API may be set.

At 626, the technique 600 may update priority based on pre-determined or custom logic. For example, priority may be set high or low based on the date that patient received the service. For example, priority may be set based weighting of multiple parameters that are related to patient information, diagnosis information, and/or procedure codes.

At 628, the technique 600 may perform asynchronous tasks such as updating providers data from NPI entry. For example, the technique 600 may recognize one or more flags that are set from missing data and/or error (e.g., from step 620, 622, 624), and connect with third-party integrations or NPI through APIs to obtain missing data or resolve error. Created order may then be saved to the server (e.g., at step 610).

Figure 7:
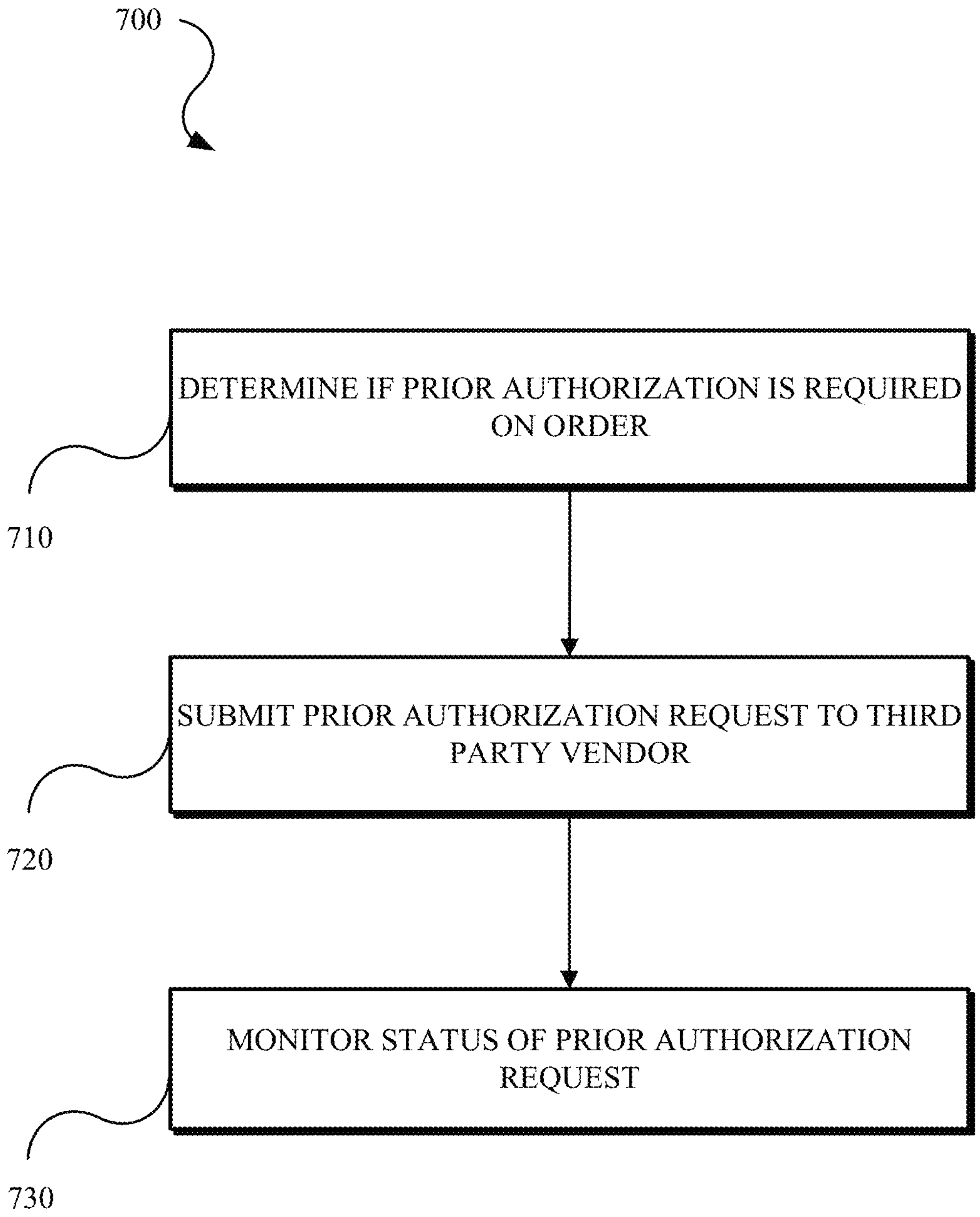
FIG. 7 is a flowchart of an example of a technique for automating prior authorizations in accordance with implementations of this disclosure.

FIG. 7 is a flowchart of an example of a technique 700 for automating prior authorizations in accordance with implementations of this disclosure. The technique 700 may be implemented by processor-based device, such as the client device 120, the computing device 200, and/or the server (e.g., the backend server such as the server application 330, any cloud server described of the system 300). The computing device 200 is representative of the type of computing device that may be present in or used in conjunction with at least some aspects of the client device 120, the server, or any other device that includes electronic circuitry.

The technique 700 may implement, be implemented by, or in conjunction with the system 100, the system 300, the technique 600, and in accordance with other implementations of this disclosure. For example, a scraper and a scraper script described in the discussion of the steps 710, 720, and 730 of the technique 700 may be the same scraper and the scraper script discussed in FIG. 3, and as such, implementations of the scraper and the scraper script discussed in FIG. 3 may apply to the steps 710, 720, and 730.

At 710, the technique 700 may determine if prior authorization is required on order. For example, the order may be a healthcare service prescribed by the medical service provider according to the technique 600 described in FIG. 6 or the technique 700 described in FIG. 7. For example, the backend server (e.g., the server application 330, backend of the software application) that stores multiple third-party vendor identification information and communicates with multiple third-party vendors may be used to determine if prior authorization is required on order.

In some implementations, determining if the prior authorization is required on the order may include utilizing a list of procedure codes that require authorization (e.g., prior authorization), in which the list of procedure codes and/or diagnosis codes may be maintained or stored in the server (e.g., the backend server such as the server application 330, any cloud server described of the system 300). For example, procedure codes may be standardized set of codes used to describe specific procedures performed by doctors and other healthcare providers in the treatment of patients. For example, procedure codes and/or diagnosis codes may include different codes such as, but not limited to, Current Procedural Terminology (CPT) codes, Healthcare Common Procedure Coding System (HCPCS) codes, and International Classification of Diseases (ICD) procedure codes (e.g., ICD-10-PCS). For example, for some third-party vendors, determining if the prior authorization is required on the order may be executed on the backend of the software application (e.g., server application) that is running on the client device and utilizes the method 500, the technique 600, the technique 700, and/or the technique 800. For example, the list of procedure codes that require authorization may be maintained or stored in the server and the procedure codes (or procedures) may be supplemented with notes and a link to the source from which the authorization information is obtained.

In some implementations, determining if the prior authorization is required on the order may include directly communicating with the third-party integrations (such as the third-party integrations 340) or the third-party vendor. For example, the technique 700, the client device that utilizes the technique 700 (e.g., runs the software application), and/or the application that utilizes the technique 700 may communicatively connect to the third-party vendor through a third-party vendor API, transmit a request for verifying whether the prior authorization is required to the third-party vendor through the third-party vendor API, and receive corresponding response from the third-party vendor through the third-party vendor API. For example, this direct communication may be executed or programmed to be automatically executed as an independent step (e.g., regardless of whether the list of prior authorization code or other ways are used) for determining if the prior authorization is required on the order. For example, this direct communication may be executed or programmed to be automatically executed in response to determining that the list of prior authorization code does not capture a procedure that is associated with the order or listed service in the order, or when there is an error in accessing the list of prior authorization code, or as an additional verification performed after the list of prior authorization code is checked.

In some implementations, determining if the prior authorization is required on the order may include utilizing a scraper script (such as the scraper script discussed in FIG. 3) to automatically find information related to prior authorization requirement, in which the scraper script includes rules and configurations that direct a scraper (e.g., automated browser) to find the information related to prior authorization requirement in one or more web portals. For example, such use of scraper script and the scraper may be executed or programmed to be automatically executed independently (e.g., regardless of whether the list of prior authorization code is used and whether direct communication with the third-party vendor is established). For example, such use of scraper script and the scraper may be executed or programmed to be automatically executed in response to determining that the list of prior authorization code does not capture a procedure that is associated with the order or listed service in the order, and/or when there is an error in accessing the list of prior authorization code, and/or when establishing direct communication with the third-party vendor is not feasible, and/or as an additional verification performed after the list of prior authorization code is checked and/or the direct communication takes place.

As described above, the scraper and the scraper script may be the same scraper and scraper script discussed in FIG. 3.

The scraper is an automated browser that can be controlled through appropriate scripts. For example, the software application (that utilizes the method 500, the technique 600, the technique 700, and/or the technique 800) or the client device that runs the software application may utilize an open-source API to automate browser functions and web scraper. The scraper may be operated in "headless mode," which makes the browser run in the background and is invisible to the user (e.g., the client). The scraper may also be operated in "full mode," which makes the browser visible, as if it were a browser opened by the user (e.g., the client). For example, the scraper may access and navigate various web portals to find desired authorization requirement information. For example, the scraper script may include code or instructions that may load and navigate particular pre-determined web portals (e.g., website, web page) of the third-party vendors or the pre-determined web portals that are associated with information (or data) in determining whether prior authorization is required on the order, and find and extract specific data related to the authorization. In some implementations, depending on a type of website or web portal where the scraping may be performed, the scraper may be operated in either the headless mode, the full mode, or the combination of both. For example, each mode may have advantages and considerations based on the type of the web portal where the scraping may be performed. For example, the scraper script may direct the scraper to automatically browse a web portal of the third-party vendor and fill out a first portion of necessary information for the prior authorization request in a headless mode or full mode, and after the portion of the necessary information is filled, direct a user to fill out a second portion of the necessary information for the prior authorization request in a full mode. For example, when some tasks are needed to be assisted by the user, the scraper may run in the full mode. For example, for tasks that need a discretion of the user or include information that cannot be entered by the headless mode completely or in accurate manner, or require further confirmation by the user, the scraper may run in the full mode to require assistance from the user. For example, the scraper script may display appropriate hints in the overlay on the webpage, so that the user knows if the action is currently being performed by the script or if the user should take an action.

At 720, the technique 700 may submit prior authorization request to third-party vendor. For example, prior authorization request may be automatically submitted to the third-party vendor after or responsive to determining that the prior authorization is required. For example, the backend be used to submit prior authorization request to third-party vendor. In some implementations, the prior authorization request may be automatically transmitted to the third-party vendor through any feasible transaction set of an electronic data interchange (EDI) standard. For example, the prior authorization request may be automatically transmitted to the third-party vendor through X12 278 transaction set of the electronic data interchange (EDI) standard.

In some implementations, the prior authorization request may be automatically transmitted to the third-party vendor using a standardized data format. For example, responsive to determining that the prior authorization request is filled and complete, the prior authorization may be automatically transmitted to the third-party vendor in JSON format. For example, if needed, the backend may parse the necessary information and/or data to extract prior authorization related data and perform a data transformation to convert the extracted data into JSON format. For example, the data transformation process in converting the extracted data into JSON format may involve mapping the information represented by the extracted data or the extracted data into JSON object properties and corresponding values, and serializing the JSON object properties into the JSON string.

In some implementations, submitting the prior authorization request to third-party vendor may include utilizing the scraper script and the scraper. For example, the scraper script and the scraper may be used to fill out necessary information or information that the scraper is capable of filling out, and it may direct or indicate the client or the user with further instructions on what actions to take (e.g., fill out rest of the information, what to do on the web page, etc.), thus relieving the client of the tedious job. For example, the software application (that utilizes the method 500, the technique 600, the technique 700, and/or the technique 800) or the client device that runs the software application may utilize the scraper script and the scraper to assist in communicating with the third-party vendor (e.g., payer, UMO, etc.) portals.

In some implementations, depending on a type of website or web portal where the scraping may be performed, the scraper may be operated in either the headless mode, the full mode, or the combination of both. For example, each mode may have advantages and considerations based on the type of the web portal where the scraping may be performed. For example, the scraper script may direct the scraper to automatically browse a web portal of the third-party vendor and fill out a first portion of necessary information for the prior authorization request in a headless mode or full mode, and after the portion of the necessary information is filled, direct a user to fill out a second portion of the necessary information for the prior authorization request in a full mode. For example, when some tasks are needed to be assisted by the user, then the scraper may run in the full mode. For example, for tasks that need a discretion of the user or include information that cannot be entered by the headless mode at all or in accurate manner, or require further confirmation by the user, the scraper may run in the full mode to require assistance from the user. For example, the scraper script may display appropriate hints in the overlay on the webpage, so that the user knows if the action is currently being performed by the script or if the user should take an action. Moreover, for example, the scraper script may use a database driver or Object-Relational Mapping (ORM) tool to connect to the SQL server (such as the SQL server database 370) and extracted data may be prepared in a standardized data format suitable for insertion into the SQL server, which may involve mapping and converting the data to the correct types, and the data may be inserted into the SQL server. For example, the server application may parse received data (e.g., response from API) into the standardized format for processing and/or storing into the SQL server in a similar manner described with respect to the scraper script. Such data in standardized data format (e.g., JSON) may be directly integrated and used directly by the backend, or pulled from the SQL server by the backend to be used in submitting or transmitting the prior authorization request to third-party vendor.

At 730, the technique 700 may monitor status of prior authorization request. For example, monitoring the status may be conducted through refreshing the request or the web page through API (e.g., open source API, third-party vendor API). For example, monitoring the status may be conducted through utilizing the scraper to automatically find the prior authorization request and save a current status in the server. For example, the scraper may automatically find the request and save the current details, and it may also make a preview of the page which can be saved as an attachment. For example, the backend may be used to monitor status of prior authorization request. In some implementations, depending on a type of website or web portal where the scraping may be performed, the scraper may be operated in either the headless mode, the full mode, or the combination of both. The implementations and examples of the web scraper and the scraper script described with respect to the step 710 and 720 may also apply to this step 730.

Figure 8:
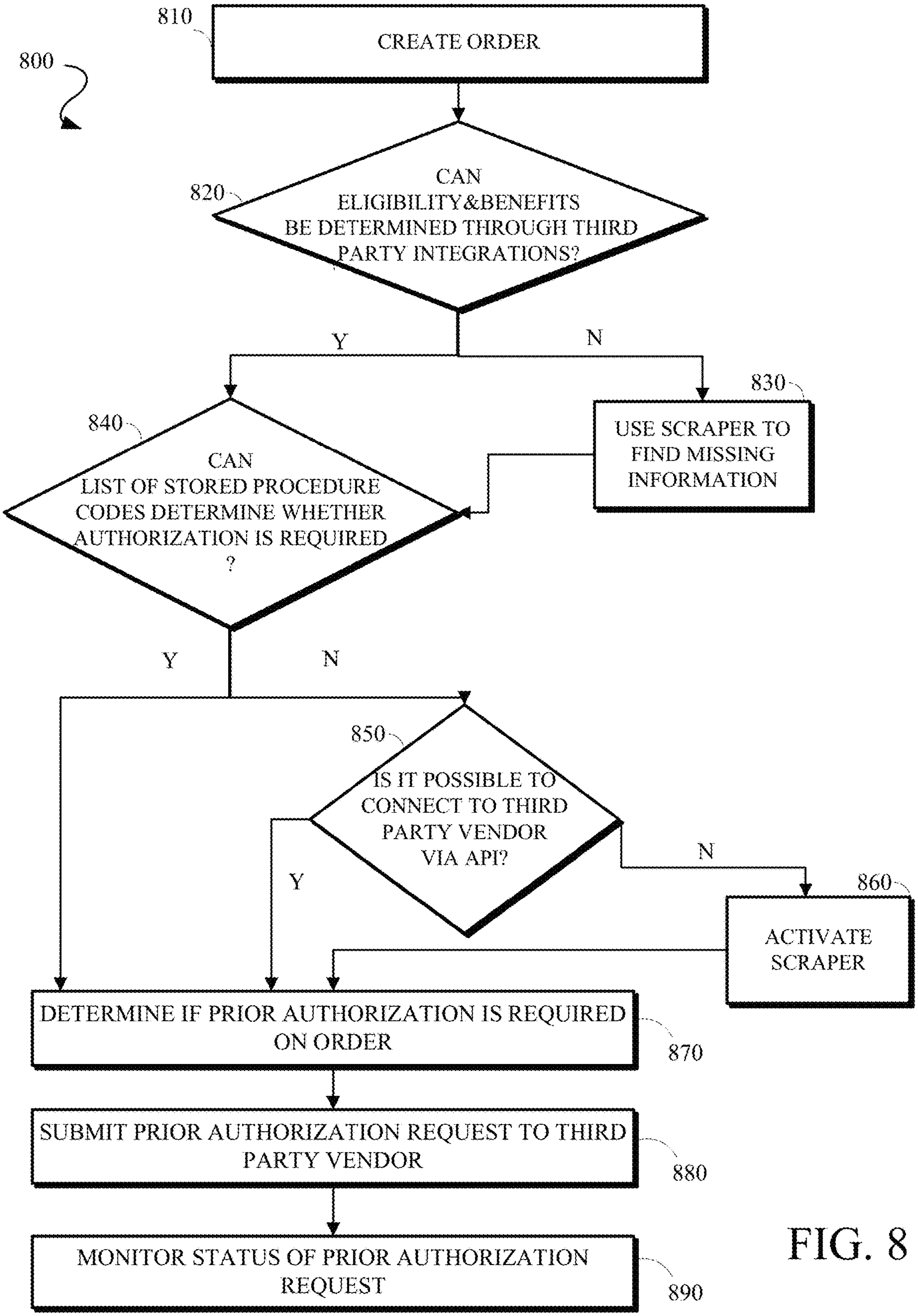
FIG. 8 is a flowchart of an example of a technique for automating prior authorizations in accordance with implementations of this disclosure.

FIG. 8 is a flowchart of an example of a technique 800 for automating prior authorizations in accordance with implementations of this disclosure. The technique 700 may be implemented by processor-based device, such as the client device 120, the computing device 200, and/or the server (e.g., the backend server such as the server application 330, any cloud server described of the system 300). The computing device 200 is representative of the type of computing device that may be present in or used in conjunction with at least some aspects of the client device 120, the server, or any other device that includes electronic circuitry.

Further, the technique 800 may implement, be implemented by, or in conjunction with the system 100, the system 300, the technique 600, the technique 700, and in accordance with other implementations of this disclosure.

At 810, the technique 800 may create the order. Since the step used here can be the same as described with regards to the order creating step 510 of the method 500 in FIG. 5, description of the step is not repeated here.

At 820, the technique 800 may determine whether eligibility and/or benefits (e.g., of a patient) pertaining to the order can be determined through third party integrations (such as the third-party integrations 340).

In some implementations, after or responsive to the creation of the order, the technique 800 may utilize EMR data from the client device, a EMR server (server that stores the EMR data that is communicatively connected to the client device), or EMR provider that provides EMR data to contact (e.g., automatically contact) the third-party vendor (e.g., via third-party vendor API) to check member eligibility and/or benefits. For example, the software application running on the client device that implements the technique 800 may (e.g., automatically) communicate (e.g., request and receive response) with the third-party vendor (e.g., via third-party vendor API) to obtain data or information pertaining to member eligibility and/or benefits based on the EMR data. For example, EMR data may be conventional EMR data which may represent comprehensive patient information including insurance details. For example, when the patients visit the client (e.g., healthcare provider), their insurance information may be collected and stored in EMR systems (e.g., application) that are running on the client device, the EMR server that is communicatively connected to the client device, and/or by the EMR provider.

In some implementations, technique 800 may utilize connections through clearinghouse services (e.g., clearinghouse services API) to automatically check member eligibility and/or benefits. For example, the clearinghouse services may be integrated with the EMIR systems to verify the patient's insurance coverage or information related to one or more healthcare insurance companies, which pertain to the created order or the information in the order. That is, direct communication (e.g., send request and receive response) between the client device (or software application that implements the technique 800) and the clearinghouse services may be used to automatically check member eligibility and/or benefits.

When it is determined that the eligibility and/or benefits (e.g., of a patient) pertaining to the order cannot be determined through third party integrations, the technique 800 may proceed to step 830.

At step 830, the scraper may be utilized (e.g., by the client device that runs the software application, by the software application, by the backend) to find the missing information. For example, when there is an error in communicating with the clearinghouse services or third-party vendors, or when it is not feasible to use the clearinghouse services or directly communicate with the third-party vendor, or when additional information that cannot be obtained through the clearinghouse services is needed, the scraper may be utilized to check for eligibility and benefits, and/or automate information input or notification regarding the search result of the eligibility and benefits. For example, when the healthcare insurance company is not a clearinghouse partner or information must be checked through the UMO (and assuming that direct communication with UMO is not feasible), the scraper may be utilized to browse web portals (e.g., UMO portals, other web portals) to check for eligibility and benefits, and/or automate information input or notification regarding the search result of the eligibility and benefits. When the missing information is found, the technique 800 may proceed to step 840. Moreover, the scraper and the scraper script may be the same scraper and scraper script discussed in FIG. 3.

When it is determined that the eligibility and/or benefits (e.g., of a patient) pertaining to the order can be determined through third party integrations, the technique 800 may proceed to step 840.

At 840, the technique 800 may determine if list of stored procedure codes can determine whether authorization (e.g., PA) is required. For example, a list of procedure codes (and/or diagnosis codes) may be maintained or stored in the server. For example, procedure codes may be standardized set of codes used to describe specific procedures performed by doctors and other healthcare providers in the treatment of patients. For example, procedure codes and/or diagnosis codes may include different codes such as, but not limited to, CPT codes, HCPCS codes, and ICD procedure codes (e.g., ICD-10-PCS). For example, for some third-party vendors, determining if the prior authorization is required on the order may be executed on the backend of the software application (e.g., server application) that is running on the client device and utilizes the method 500, the technique 600, the technique 700, and/or the technique 800. For example, the list of procedure codes that require authorization may be maintained or stored in the server and the procedure codes (or procedures) may be supplemented with notes and a link to the source from which the authorization information is obtained.

When it is determined that the list of stored procedure codes cannot determine whether or not the authorization (e.g., PA) is required, the technique 800 proceeds to step 800 to activate the scraper. Then the technique 800 proceeds to step 870 to determine that the prior authorization is required utilizing the scraper. Since the step used here can be the same as described with regards to determination step 710 of the technique 700 in FIG. 7, description of the step is not repeated here.

When it is determined that the list of stored procedure codes can determine whether or not the authorization (e.g., prior authorization) is required, it proceeds to step 710 to determine that the prior authorization is required accordingly.

Even though steps 840, 850, and 860 are ordered in sequence beginning from 840 and proceeding to 850 and 860 accordingly, steps 840, 850, 860 may be implemented in any sequence or combination, and independently without relying on each other.

At 870, the technique 800 may determine that if the prior authorization is required on the order. Since the step used here can be the same as described with regards to the step 710 of the technique 700 in FIG. 7, description of the step is not repeated here.

At 880, the technique 800 may submit the prior authorization request to third party vendor. Since the step used here can be the same as described with regards to the step 720 of the technique 700 in FIG. 7, description of the step is not repeated here.

At 890, the technique 800 may monitor a status of the prior authorization request. Since the step used here can be the same as described with regards to the step 730 of the technique 700 in FIG. 7, description of the step is not repeated here.

It should be noted that the applications and implementations of this disclosure are not limited to the examples, and alternations, variations, or modifications of the implementations of this disclosure can be achieved for any computation environment.

It may be appreciated that various changes can be made therein without departing from the spirit and scope of the disclosure. Moreover, the various features of the implementations described herein are not mutually exclusive. Rather any feature of any implementation described herein may be incorporated into any other suitable implementation.

The implementations of this disclosure can be described in terms of functional block components and various processing operations. Such functional block components can be realized by a number of hardware or software components that perform the specified functions. For example, the disclosed implementations can employ various integrated circuit components (e.g., memory elements, processing elements, logic elements, look-up tables, and the like), which can carry out a variety of functions under the control of one or more microprocessors or other control devices. Similarly, where the elements of the disclosed implementations are implemented using software programming or software elements, the systems and techniques can be implemented with a programming or scripting language, such as C, C++, Java, JavaScript, assembler, or the like, with the various algorithms being implemented with a combination of data structures, objects, processes, routines, or other programming elements.

Functional aspects can be implemented in algorithms that execute on one or more processors. Furthermore, the implementations of the systems and techniques disclosed herein could employ a number of conventional techniques for electronics configuration, signal processing or control, data processing, and the like. The words "mechanism" and "component" are used broadly and are not limited to mechanical or physical implementations, but can include software routines in conjunction with processors, etc. Likewise, the terms "system" or "tool" as used herein and in the figures, but in any event based on their context, may be understood as corresponding to a functional unit implemented using software, hardware (e.g., an integrated circuit, such as an ASIC), or a combination of software and hardware. In certain contexts, such systems or mechanisms may be understood to be a processor-implemented software system or processor-implemented software mechanism that is part of or callable by an executable program, which may itself be wholly or partly composed of such linked systems or mechanisms.

Implementations or portions of implementations of the above disclosure can take the form of a computer program product accessible from, for example, a computer-usable or computer-readable medium. A computer-usable or computer-readable medium can be a device that can, for example, tangibly contain, store, communicate, or transport a program or data structure for use by or in connection with a processor. The medium can be, for example, an electronic, magnetic, optical, electromagnetic, or semiconductor device.

Other suitable mediums are also available. Such computer-usable or computer-readable media can be referred to as non-transitory memory or media, and can include volatile memory or non-volatile memory that can change over time. The quality of memory or media being non-transitory refers to such memory or media storing data for some period of time or otherwise based on device power or a device power cycle. A memory of an apparatus described herein, unless otherwise specified, does not have to be physically contained by the apparatus, but is one that can be accessed remotely by the apparatus, and does not have to be contiguous with other memory that might be physically contained by the apparatus.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system, comprising:

a backend server including a memory and a processor configured to execute instructions stored in the memory to:

determine, using first information obtained based on the backend server executing first scripting instructions executable to cause a web browser running at a client device in communication with the backend server to scrape data from a first web source associated with a third-party vendor, whether prior authorization is required on an order created by the backend server and associated with a healthcare service prescribed by a medical service provider, wherein, based on the first web source including all of the first information, the first scripting instructions operate in a headless mode in which the web browser scrapes the first web source to obtain the first information while running in a background of the client device and while the web browser is invisible to a user of the client device; and responsive to a determination that the prior authorization is required on the order, submit, using second information obtained based on the backend server executing second scripting instructions executable to cause the web browser running at the client device to scrape data from a second web source, a prior authorization request in a standardized data format to the third-party vendor, wherein, based on the second web source including only some of the second information, the second scripting instructions operate in a full mode to configure the web browser to obtain user input in connection with the scraping of the second web source, wherein the full mode corresponds to the web browser scraping the second web source while the web browser and the second web source are visible to the user of the client device, wherein the second information is obtained based on the scraping of the second web source and based on the user input, wherein the backend server outputs to the client device data to render an overlay on the second web source while the web browser is visible to the user of the client device, and wherein the overlay indicates whether an action is currently being performed by the second scripting instructions or whether the user should take an action.

2. The system of claim 1, wherein, to determine whether the prior authorization is required on the order, the processor is configured to execute the instructions to:

utilize a list of procedure codes that require authorization, wherein the list of procedure codes is stored in a data store of the backend server.

3. The system of claim 1, wherein, to determine whether the prior authorization is required on the order, the processor is configured to execute the instructions to:

connect to the first web source through a third-party vendor application programming interface (API);

transmit a request for verifying whether the prior authorization is required to the third-party vendor through the third-party vendor API; and receive a corresponding response from the third-party vendor through the third-party vendor API.

4. The system of claim 1, wherein, to determine whether the prior authorization is required on the order, the processor is configured to execute the instructions to:

determine whether connecting to the first web source through a third-party vendor application programming interface (API) can be achieved; and responsive to a determination that connecting to the first web source through the third-party vendor API cannot be achieved, utilize the first scripting instructions to automatically find information related to the prior authorization.

5. The system of claim 1, wherein, to submit the prior authorization request in the standardized data format to the third-party vendor, the processor is configured to execute the instructions to:

automatically transmit the prior authorization request to the third-party vendor through a X12 278 transaction set of an electronic data interchange (EDI) standard.

6. The system of claim 1, wherein, to submit the prior authorization request to the third-party vendor, the processor is configured to execute the instructions to:

utilize the second scripting instructions to:

automatically browse the second web source and fill out a first portion of necessary information for the prior authorization request; and after the first portion of the necessary information is filled, direct the user via the overlay to fill out on the second web source, as the user input, a second portion of the necessary information for the prior authorization request.

7. The system of claim 1, wherein the processor is configured to execute the instructions to:

monitor a status of the prior authorization request.

8. A method, comprising:

determining, using first information obtained based on a backend server executing first scripting instructions executable to cause a web browser running at a client device in communication with the backend server to scrape data from a first web source associated with a third-party vendor, whether prior authorization is required on an order created by the backend server and associated with a medical service provider, wherein, based on the first web source including all of the first information, the first scripting instructions operate in a headless mode in which the web browser scrapes the first web source to obtain the first information while running in a background of the client device and while the web browser is invisible to a user of the client device; and responsive to determining that the prior authorization is required on the order, submitting, using second information obtained based on the backend server executing second scripting instructions executable to cause the web browser running at the client device to scrape data from a second web source, a prior authorization request in a standardized data format to the third-party vendor, wherein, based on the second web source including only some of the second information, the second scripting instructions operate in a full mode to configure the web browser to obtain user input in connection with the scraping of the second web source, wherein the full mode corresponds to the web browser scraping the second web source while the web browser and the second web source are visible to the user of the client device, wherein the second information is obtained based on the scraping of the second web source and based on the user input, wherein the backend server outputs to the client device data to render an overlay on the second web source while the web browser is visible to the user of the client device, and wherein the overlay indicates whether an action is currently being performed by the second scripting instructions or whether the user should take an action.

9. The method of claim 8, wherein determining whether the prior authorization is required on the order comprises:

utilizing a list of procedure codes that require authorization.

10. The method of claim 8, wherein determining whether the prior authorization is required on the order comprises:

connecting to the first web source through an application programming interface (API) such that a request for verifying whether the prior authorization is required can be transmitted and corresponding response can be received through the API.

11. The method of claim 8, wherein determining whether the prior authorization is required on the order comprises:

utilizing the first scripting instructions to automatically find information related to the prior authorization, wherein the first scripting instructions include rules and configurations to find the information related to the prior authorization in one or more web portals associated with the first web source.

12. The method of claim 8, wherein submitting the prior authorization request in the standardized data format to the third-party vendor comprises:

automatically transmitting the prior authorization request to the third-party vendor in a JSON data format.

13. The method of claim 8, wherein submitting the prior authorization request to the third-party vendor comprises:

automatically browsing the second web source and filling out a first portion of necessary information for the prior authorization request; and after the first portion of the necessary information is filled, directing the user via the overlay to fill out on the second web source, as the user input, a second portion of the necessary information for the prior authorization request.

14. The method of claim 8, comprising:

monitoring a status of the prior authorization request by utilizing a scraper script and a scraper to automatically find the prior authorization request and saving a current status.

15. A non-transitory computer-readable medium storing instructions operable to cause one or more processors to perform operations comprising:

determining, using first information obtained based on first scripting instructions executable to cause a web browser running at a client device to scrape data from a first web source associated with a third-party vendor, whether prior authorization is required on an order associated with a medical service provider, wherein, based on the first web source including all of the first information, the first scripting instructions operate in a headless mode in which the web browser scrapes the first web source to obtain the first information while running in a background of the client device and while the web browser is invisible to a user of the client device; and responsive to determining that the prior authorization is required on the order, submitting, using second information obtained based on second scripting instructions executable to cause the web browser running at the client device to scrape data from a second web source, a prior authorization request to the third-party vendor, wherein, based on the second web source including only some of the second information, the second scripting instructions operate in a full mode to configure the web browser to obtain user input in connection with the scraping of the second web source, wherein the full mode corresponds to the web browser scraping the second web source while the web browser and the second web source are visible to the user of the client device, wherein the second information is obtained based on the scraping of the second web source and based on the user input, wherein the second scripting instructions output to the client device data to render an overlay on the second web source while the web browser is visible to the user of the client device, and wherein the overlay displays hints comprising whether an action is currently being performed by the second scripting instructions or whether the user should take an action.

16. The non-transitory computer-readable medium of claim 15, wherein determining whether the prior authorization is required on the order comprises:

transmitting a request for verifying whether the prior authorization is required to the third-party vendor through a third-party vendor application programming interface (API); and receiving a corresponding response from the third-party vendor through the third-party vendor API.

17. The non-transitory computer-readable medium of claim 15, wherein determining whether the prior authorization is required on the order comprises:

determining whether connecting to the third-party vendor through a third-party vendor application programming interface (API) can be achieved.

18. The non-transitory computer-readable medium of claim 15, wherein submitting the prior authorization request to the third-party vendor comprises:

transmitting the prior authorization request to the third-party vendor via an electronic data interchange (EDI) standard.

19. The non-transitory computer-readable medium of claim 15, wherein submitting the prior authorization request to the third-party vendor comprises:

executing the second scripting instructions to:

automatically browse a web portal of the second web source for a first portion of necessary information for the prior authorization request; and after the first portion of the necessary information is filled, direct a user via the overlay to fill out on the second web source, as the user input, a second portion of the necessary information for the prior authorization request.

20. The non-transitory computer-readable medium of claim 15, the operations comprising:

monitoring the prior authorization request to determine a current status of the prior authorization request.

* * * * *